(12) United States Patent
Tarlano

(10) Patent No.: US 6,975,702 B2
(45) Date of Patent: *Dec. 13, 2005

(54) METHOD FOR INACTIVATING CANCER CELLS IN A HUMAN BODY AND APPARATUS

(76) Inventor: John Paul Tarlano, 6912 Sydenstricker Rd., Springfield, VA (US) 22152

( * ) Notice: Subject to any disclaimer, the term of this patent is extended or adjusted under 35 U.S.C. 154(b) by 53 days.

This patent is subject to a terminal disclaimer.

(21) Appl. No.: 10/608,105

(22) Filed: Jun. 30, 2003

(65) Prior Publication Data

US 2004/0264639 A1    Dec. 30, 2004

(51) Int. Cl.[7] .................................................. A61N 5/10
(52) U.S. Cl. ................................................... 378/65
(58) Field of Search ..................... 378/64, 65; 604/20, 604/21; 607/96, 100

(56) References Cited

U.S. PATENT DOCUMENTS

| | | | | |
|---|---|---|---|---|
| 4,622,952 A | * | 11/1986 | Gordon | 600/10 |
| 5,044,006 A | * | 8/1991 | Cyrulnik | 378/145 |
| 5,690,109 A | * | 11/1997 | Govind et al. | 600/411 |

* cited by examiner

*Primary Examiner*—Edward J. Glick
*Assistant Examiner*—Thomas R. Artman

(57) ABSTRACT

An X-ray apparatus for inactivating cancer cells in a human body is disclosed. The X-ray apparatus has four X-ray guns. Each of the four X-ray guns generating a separate frequency of an X-ray burst. A cancer cell inactivation method is also disclosed. The human body is irradiated with a series of bursts of X-rays, the X-ray bursts having a series of frequencies tuned to energize four different amino acid bases of DNA of each of the cancer cells.

2 Claims, 1 Drawing Sheet

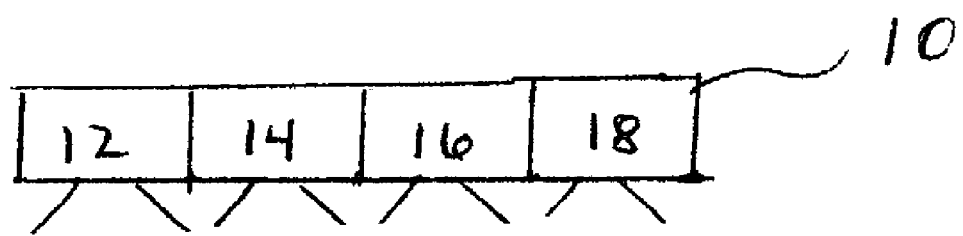

METHOD FOR INACTIVATING CANCER CELLS IN A HUMAN BODY AND APPARATUS

The present invention relates to a method and apparatus for inactivating cancer cells in a human body, by means of a series of x-ray pulses. The present method targets just the cancer cells.

In the past, cancer cells were targeted for destruction by means of various chemicals. However that method has proven to be produce unwanted side effects in the human body. The chemicals do not target just the cancer cells.

The present invention relates to a method and apparatus for targeting the cancer cells by the use of x-ray pulses having frequencies that target a sub-sequence of amino acid bases of DNA of the cancer cells.

Cancer cells and matching normal cells are taken from a human body. The sequence of amino acid bases in the cancer cells, and in the normal cells, are determined. Again, the cancer cells and the normal cells are analyzed to determine a sequence of bases in the cancer cells and in the normal cells. The sequence of amino acid bases in the cancer cells and in the normal cells are compared, to identify a sub-subsequence of bases that are in the cancer cells but that are not in the sequence of bases in the DNA of the normal cells. A series of bases in the sub-sequence of bases in the cancer cells is selected.

The selected series of amino acid bases in the sub-sequence of bases in the cancer cells located in a human body, are energized by the x-ray pulses and the DNA of the irradiated cancer cells are broken apart. Thus the cancer cells are prevented from dividing. That is, the DNA chain in each of the irradiated cancer cells located in a human body, are destroyed.

In a preferred embodiment, a series of amino acid bases of a section of a DNA of a cancer cell, is determined. A series of approximately 10 bases is determined.

An X-ray burst having a frequency of 9.25 (10 exp 16) cycles per second, corresponding to 383 electron volts, is used to energize a T amino acid base in the series of bases. An X-ray burst having a frequency corresponding to 268 electron volts, is used to energize a G base in the series of bases. An X-ray burst having a frequency corresponding to 283 electron volts, is used to energize an A amino acid base in the series of bases. An X-ray burst having a frequency of corresponding to 392 electron volts, is used to energize a C amino acid base in the series of bases.

The series of bursts of X-rays is made to irradiate a human body, that has cancer cells, for a time duration such as 100 seconds. Ten bases are covered with a 10 second time interval between two successive X-ray bursts.

The above 383 and 392 electron volt frequencies of x-ray bursts are absorbed by nitrogen atoms of the T and C amino acid bases of the cancer cells. The above 283 and 268 electron volt frequencies of x-ray bursts are absorbed by carbon atoms of the A and G amino acid bases of the cancer cells.

Nitrogen-hydrogen type hydrogen bonds, made by T and C amino acid bases of the DNA of the cancer cells, are effected by the described X-ray bursts. Carbon-hydrogen type hydrogen bonds, made with A and G amino acid bases of the DNA of the cancer cells, are effected by the described X-ray bursts. Hydrogen bonds with the amino acid bases of the virus are effected by the X-ray bursts. As is well known in the art, an A base is Adonine, a T base is Thymine, a G base is Guanine and a C base is Cytosine.

The X-ray bursts are generated by four X-ray guns of an X-ray apparatus. The X-ray dose level from the X-ray guns is kept low compared with a normal chest x-ray level.

SUMMARY OF THE INVENTION

An X-ray apparatus for inactivating cancer cells in a human body comprising four X-ray guns, each of the four X-ray guns generating a separate frequency of an X-ray burst, a first separate frequency tuned to energize an amino acid base A, a second separate frequency tuned to energize an amino acid base G, a third separate frequency tuned to energize an amino acid base T, and a fourth separate frequency tuned to energize an amino acid base C.

DESCRIPTION OF THE DRAWING

FIG. 1 is a perspective view of apparatus having four X-ray guns, the apparatus for irradiating a human body.

DESCRIPTION OF THE PREFERRED EMBODIMENT

In the preferred embodiment, cancer cells are withdrawn from region of a human being. The region is one that has both cancer cells and normal cells. The DNA of the cancer cells is analyzed. A sequence of amino acid bases in the DNA of the cancer cells is determined. Also, the normal cells are analyzed. A sequence of amino acid bases in the DNA of the normal cells is determined.

The sequence of amino acid bases in the DNA of the normal cells is compared to the sequence of amino acid bases in the DNA of the cancer cells. A sub-sequence of bases of DNA only located in the DNA of the cancer cells, is identified. That is, a sub-sequence of bases of DNA, that is not in the DNA of the normal cells, is identified. A series of bases in the sub-sequence of bases of DNA of the cancer cells is also identified.

A series of frequencies for a series of x-ray pulses that will energize a series of bases in the sub-sequence of bases in the cancer cells, is determined.

In patent application Ser. No. 10/445,614 filed May 27, 2003, the x-ray frequency to energize each T amino acid base, G amino acid base, A amino acid base and C amino acid base, of a part on RNA of a virus, is given. The teachings of that patent application are incorporated herein by reference. Further, in a similar manner as taught in that patent application, a human being is irradiated by a series of x-ray pulses whose frequencies energize the selected series of bases in the sub-sequence of bases in a cancer cell. The cancer cells are thus destroyed.

For example, if the series of bases in the sequence of bases is AATGCATGCA, the frequencies of the ten x-ray pulses, in electron volts, are 283, 283, 383, 268, 392, 283, 383, 268, 392 and 283.

An apparatus shown in patent application Ser. No. 10/445,614 is used to irradiate a human body that has cancer cells. The irradiated cancer cells should identical to the cancer cells that have been analyzed, so the irradiated cancer cells have the same series of bases that were in the analyzed cancer cells. The irradiation should have with the series of x-ray pulses whose frequencies are selected for the series of bases in the sub-sequence of bases in the irradiated cancer cells.

The apparatus has four x-ray guns. The four x-ray guns are activated to produce a series of x-ray pulses whose frequencies energize the selected series of bases of cancer cells, in the human body, that are being irradiated. Again the irradiated cancer cells are identical to the analyzed cancer cells. Each base in the selected series of bases in the sub-sequence of bases is energized by an x-ray pulses of the series of x-ray pulses.

An x-ray pulse having a frequency of 9.25(10 exp 16) cycles per second, corresponding to 383 electron volts, is used to energize a T amino acid base in the series of DNA bases. An x-ray pulse having a frequency corresponding to 268 electron volts is used to energize an amino acid base in the series of DNA bases. An x-ray pulse having a frequency corresponding to 283 electron volts; is used to energize an A amino acid base in the series of DNA bases. An x-ray pulse having a frequency corresponding to 392 electron volts is used to energize a C amino acid base in the series of DNA bases.

FIG. 1 shows an X-ray apparatus 10. The x-ray apparatus 10 has an X-ray gun 12, an X-ray gun 14, an X-ray gun 16, and an X-ray gun 18. Each X-ray gun generates a burst of X-rays having a separate selected frequency. X-ray gun 12 generates a burst of X-rays having a frequency of 383 electron volts. X-ray gun 14 generates a burst of X-rays having a frequency of 392 electron volts. X-ray gun 16 generates a burst of X-rays having a frequency of 283 electron volts. X-ray gun 18 generates a burst of X-rays having a frequency of 267 electron volts.

The X-ray machine 10 irradiates a human body 20 with a series of ten bursts of X-rays, each burst having a frequency selected to hit an amino acid base of section of DNA of each of the cancer cells in a human body 10.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An X-ray apparatus for inactivating cancer cells in a human body, comprising four X-ray guns, each of the four X-ray guns generating a separate frequency of an X-ray burst, a first separate frequency tuned to energize an amino acid base A, a second separate frequency tuned to energize an amino acid base G, a third separate frequency tuned to energize an amino acid base T, and a fourth separate frequency tuned to energize an amino acid base C.

2. A method of inactivating cancer cells in a human body, comprising:
   (a) determining a sub-sequence of bases in DNA of cancer cells that are taken from a region of the human body, the sub-sequence of bases not being in DNA of normal cells that are also taken from the region of the human body; and
   (b) irradiating a selected series of bases that are in the sub-sequence of bases of DNA of the cancer cells with a series of x-ray pulses, the irradiated cancer cell being in the human body, the irradiated cancer cells being identical to the cancer cells taken from the human body, the series of x-ray pulses having a sequence of frequencies that energize the series of bases of the DNA of the cancer cells being irradiated.

\* \* \* \* \*